United States Patent [19]

Thompson

[11] Patent Number: 5,181,419
[45] Date of Patent: Jan. 26, 1993

[54] SAMPLING OF DRILLING MUD

[75] Inventor: Martin Thompson, Cambridge, England

[73] Assignee: Schlumberger Technology Corporation, Houston, Tex.

[21] Appl. No.: 616,443

[22] Filed: Nov. 20, 1990

[30] Foreign Application Priority Data

Nov. 27, 1989 [GB] United Kingdom ............... 8926778

[51] Int. Cl.$^5$ .................. G01N 35/00; E21B 49/00
[52] U.S. Cl. .................................. 73/153; 73/863.01
[58] Field of Search ............... 73/153, 863.01, 434, 73/53, DIG. 8; 137/561

[56] References Cited

U.S. PATENT DOCUMENTS

| | | | |
|---|---|---|---|
| 2,342,273 | 2/1944 | Hayward | 73/153 |
| 3,004,544 | 10/1961 | Guptill, Jr. | 73/434 |
| 3,422,674 | 1/1969 | Schroeter | 73/153 |
| 3,435,663 | 4/1969 | de Lamballerie | 73/38 |
| 3,911,741 | 10/1975 | Rochon et al. | 73/153 |
| 4,321,465 | 3/1982 | Stover et al. | 250/255 |
| 4,369,655 | 1/1983 | Scearce | 73/153 |
| 4,677,851 | 7/1987 | McAuley | 73/434 |
| 4,807,469 | 2/1989 | Hall | 73/155 |
| 4,860,836 | 8/1989 | Gunther | 73/153 |
| 4,904,603 | 2/1990 | Jones et al. | 73/153 |

FOREIGN PATENT DOCUMENTS

| | | |
|---|---|---|
| WO88/02855 | 4/1988 | European Pat. Off. . |
| 2212611 | 7/1989 | United Kingdom . |
| 2226135 | 6/1990 | United Kingdom . |

Primary Examiner—Hezron E. Williams
Assistant Examiner—Michael Brock
Attorney, Agent, or Firm—John J. Ryberg

[57] ABSTRACT

A sample flow of drilling mud is taken via a pipe 14 from a shale shaker tank 10 and passed into a container 15 with a vigorous stirrer 17 and having a capacity of typically 0.40 m$^3$. The sample flow rate and size of the container are sufficient to permit analysis of samples taken at 15 minute intervals via a pipe 18 and valve 19, without aliasing information in the resulting data. For eight hour sampling an intermittent flow is taken from the container 15 into another agitated container 21 via a pipe 26 with a valve 27 which is open only for two seconds in every minute. Analysis samples are taken via a pipe 22 and a valve 23 and the residence time in the tanks 15 and 21 is sufficient to prevent aliasing in the information acquired by eight hour sampling and analysis.

14 Claims, 6 Drawing Sheets

SAMPLING OF DRILLING MUD

This invention relates to a method of sampling drilling mud and to apparatus for use in carrying out the method.

It has long been the practice to sample the return mud from a borehole and to analyse it in order to keep the mud composition in accordance with that specified by the well operator, in particular to maintain the correct mud density to give the correct pressure for containing formation pressures at the bottom of the well. Such analysis is normally performed only infrequently, e.g. three times per 24 hour day. However it has already been proposed in GB-A 2 212 611 to effect frequent analyses, e.g. several per hour and moreover to analyse both the mud being pumped into the drill string and the mud emerging from the borehole annulus. Information as to the drilling lithology can then be obtained by comparing the results of the analyses, taking into account the time lag between pumping in the mud and its re-emergence from the annulus.

GB-A 2 212 611 is concerned essentially with analysis of solids content, including the use of ion chromatography to determine weight of electrolyte. However no indication is given as to the times at which the analyses are actually performed, specifically whether they are performed in real time or historically. Real time analysis implies that the analyses are effected at the same rate as the samples are taken and that the data is available for each sample with a delay no more than, or little more than that imposed by the time taken to complete an analysis.

The present invention stems firstly from an appreciation that it is possible to obtain detailed information regarding the strata being drilled from the circulating mud by frequent analysis—in the limit analysis at the shortest possible intervals consistent with the time taken to complete an analysis. Secondly it has been appreciated that infrequent analysis (indeed even analysis as frequent as is envisaged in GB-A 2 212 611) can lead to spurious results. This arises from a phenomenon known as aliasing.

Aliasing is well understood in totally different areas but has not heretofore been considered in mud analysis. A well known example of aliasing is seen in old films of say a stage coach where the wheels of a forward moving vehicle appear to rotate backwards. The reason for this is that the frames of the film are samples of the continuously moving image and the samples are too infrequent to convey the movement correctly. Say the spokes of a wheel are advancing by 9/10ths of the angle between spokes between successive frames. The effect, when the film is shown, is that the spokes appear to be moving back by 1/10th of the angle between spokes, so that the wheel appears to be rotating slowly backwards. The slow backward rate of rotation is an alias of the true forward rate.

Aliasing has been analysed extensively in relation to the sampling of electrical signals. FIG. 1 of the accompanying drawings shows at (a) a square-wave signal 10 and black dots 11 show instants at which the signal is regularly sampled. The intervals between samples have been chosen short compared with the period P of the signal and it can be seen that the samples give a reasonably reliable approximation to the shape of the signal. However the same signal 10 is shown at (b) sampled (dots 12) much less frequently—one sample per 1.125 P.

The samples 12 do not represent the signal 10 but appear to represent a very much more slowly changing signal 13 (waveform (c)) which is the alias of the time signal 10. Mathematical analysis shows that, in order to represent a signal component of a given frequency $f=1/P$ by means of samples thereof, the samples must be taken with a frequency of at least $2f$.

The problem with aliasing is that it creates spurious information. In order to avoid this there are two remedies available. The first is to increase the frequency of sampling but this is not always possible, e.g. when it is restricted by the speed with which the samples can be processed. This is precisely the situation which can occur in sampling mud.

The second remedy, in the case of electrical signal is to filter the signal before it is sampled so as to eliminate the higher frequency components which will, if present, lead to aliasing, while leaving lower frequency components which can be represented correctly by sampling at the sampling rate adopted. This is done by passing the signal through a low-pass filter which cuts out frequencies above half the sampling rate.

Unfortunately this cannot be done when sampling mud. There is no continuous signal to filter. The object of the present invention is to provide a method and an apparatus which overcome the problem hereby posed.

The invention provides a method of sampling drilling mud wherein a sample flow taken from a selected point in the mud circuit is fed into an agitated container having a capacity such that the residence time of an increment of sample flow is significant and wherein samples are taken from the container at regular intervals.

The container performs the function of averaging the sample flow, thereby at least partially overcoming the aliasing. What constitutes a significant residence time (explained below) will depend upon the sampling rate but it will be a time sufficient to eliminate aliasing or at least make a real reduction in aliasing. For low sampling rates, e.g. 8 hour sampling, it may be impossible to achieve a long enough residence time in a single container of acceptable size and the invention therefore further provides for use of a series of two or more containers. Various magnitudes can be determined from the following considerations.

The size of the samples will be determined by whatever analysis is to be effected, whether ion chromatography and/or other measurements—the invention is not concerned with the nature of the analysis which can be conventional in itself.

The agitated container must be large enough for its averaging action not to be noticeably perturbed by withdrawing the samples. On the other hand, the tank cannot be too large since space on a drilling rig is at a premium and the extra mud is expensive. In practice a size of 0.5 m$^3$ may be suitable.

The rate of the sample flow is then determined by the degree of averaging required.

As a molecule enters a mixing system it will remain in the system for a certain period of time, known as the residence time, before leaving the system. For all molecules, there will be a probability distribution of residence times according to the system and a mean residence time T which is equal to the system volume V divided by the throughput flowrate Q. The residence time distribution is given by the system response to a step change in input. Alternatively, if a Dirac-delta function is input in the system, then the response is known as the impulse response. The time integral of the impulse response gives the residence time distribution function.

For a single mixing tank, the impulse response f(t) is:

$$f(t) = 1/T \exp(-t/T) \quad (1)$$

which therefore has a frequency response F(w) at a certain frequency w given by:

$$F(w) = 1/(1 + jwT) \quad (2).$$

The magnitude of the frequency response of a single tank with a residence time T and at a frequency w is therefore:

$$|F(w)| = 1/(1 + w^2 T^2)^{\frac{1}{2}} \quad (3).$$

The higher the frequency w, the lower the response F(w). So, for high frequencies, the tank is acting as a filter. Even at the cut-off frequency, the amplitude of the filtered signal is not zero, but has small value which is acceptable in practice. We can arbitarily choose the degree of attenuation a to be provided by the filter at the cut-off that the frequency $w_c$, say an attenuation of 10 for example, so frequency response F(w) at the frequency $w_c$ and above will not cause any aliasing. Of the signal. Therefore, at the cut-off frequency:

$$|F(w_c)| \leq 1/\alpha \quad (4).$$

By combining equations (3) and (4), we obtain:

$$1 + w_c^2 T^2 \geq \alpha^2 \quad (5)$$

or:

$$T \geq (\alpha^2 - 1)^{\frac{1}{2}}/w_c \quad (6).$$

Since the residence time T is equal to the volume of the tank V divided by the throughput flowrate Q, we obtain from (6):

$$V/Q \geq (\alpha^2 - 1)^{\frac{1}{2}}/w_c \quad (7)$$

In addition, it is well known in signal processing that, in order not to introduce aliaising, a signal sampled at a frequency $w_s$ must not contain any frequency larger than $w_s/2$. If the mud is sampled at a frequency $w_s$, the filter constituted by the mud container must eliminate, or sufficiently attenuate, the frequency components corresponding to frequencies larger than $w_s/2$. The latter is the cut-off frequency $w_c$ of the mud container and therefore by replacing $w_c$ by $w_s/2$ in equation (7):

$$V/Q \geq 2(\alpha^2 - 1)^{\frac{1}{2}}/w_s \quad (8)$$

Knowing the sample frequency (samples taken once every 15 minutes for example) and the acceptable attenuation a (say 10 for example), equation (8) allows one to choose acceptable values for V and Q.

It can readily be understood that increasing the sample flow rate reduces the averaging action, i.e. shifts the cut-off frequency upwardly. To obtain a high measure of averaging, when the analysed samples are taken infrequently, e.g. only 2 or 3 times a day, may pose problems. It implies a very small sample flow rate and a large container. There has to be a reasonable rate of flow into the container to avoid clogging which is especially liable to occur on account of the thixotropic nature of drilling mud.

Hence the development of the invention according to which a series of two or more containers is used.

For n mud container in cascade, each having a frequency response $F_n(w)$ and a residence time $T_n$, the global frequency response F(w) of the system is:

$$F(w) = FPV1PV(w) \cdot F_2(w) \ldots F_n(w)$$

A small effective sample flow rate may however be achieved by taking intermittent samples of the flow at a rate sufficiently high to avoid the creation of aliasing. Preferably the flow from a first container into a second container is effected by intermittent, frequent samples, e.g. samples of a few seconds duration around every minute.

The invention further provides an apparatus for sampling drilling mud comprising means for taking a sample flow from a point in the mud circuit and feeding the sample flow into a container having a capacity such that the residence time of an increment of sample flow is significant, means for agitating the mud in the container, and means for taking samples from the container at regular intervals.

The invention will be described in more detail, by way of example, with reference to the accompanying drawings, in which.

Figure 1:
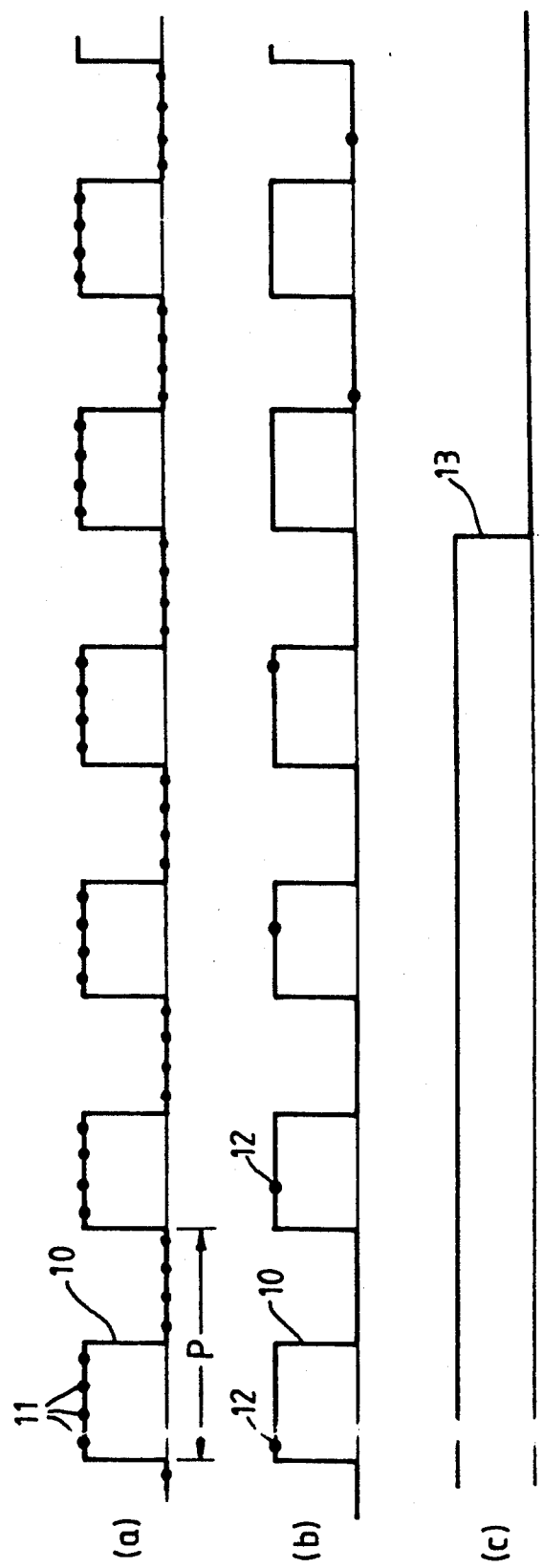
FIG. 1 is an explanatory diagram already considered in explaining aliasing.
Figure 2:
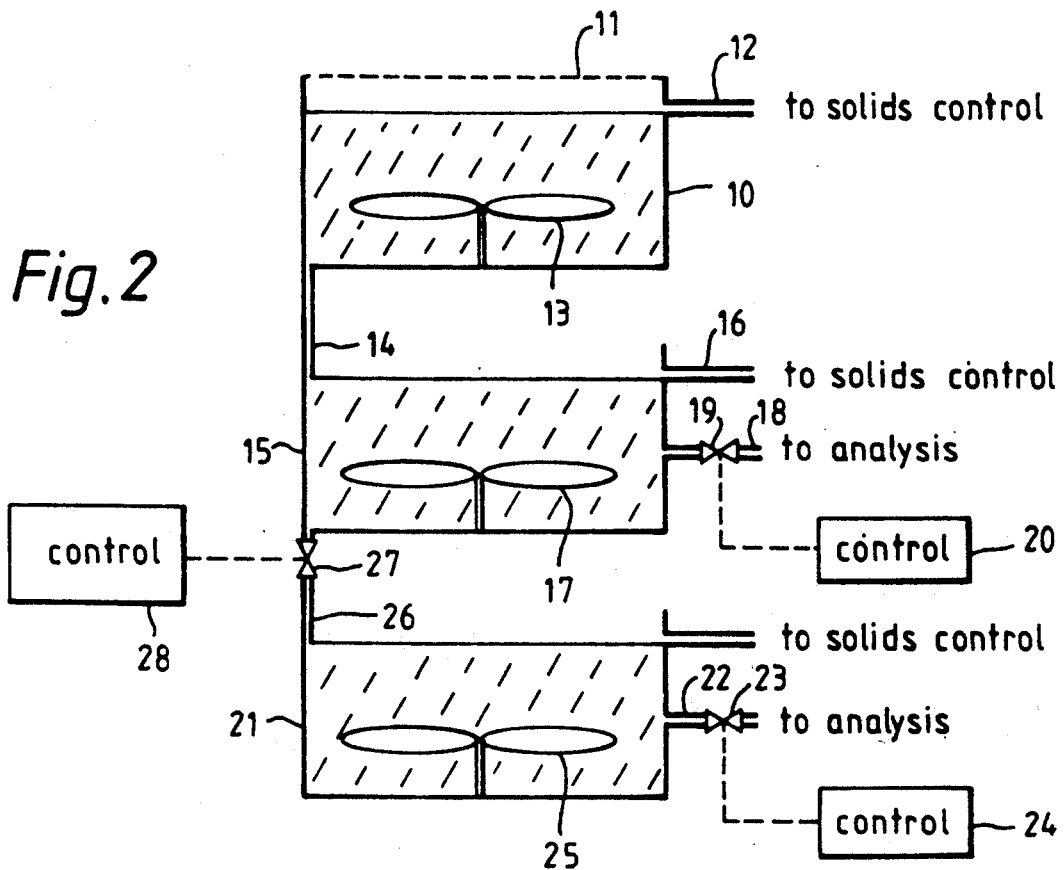
FIG. 2 is a diagram of apparatus embodying the invention.

In FIG. 2 it is assumed that the mud to be sampled is the mud returning via the well annulus. Accordingly the first samples are drawn from the conventional shale shaker tank 10 from which the major part of the mud overflows to the conventional solids control plant and active tank, where its composition is adjusted and whence it is pumped back to the drill string. On the other hand the tank 10 could equally well be the active tank or a tank placed in the line from the active tank to the drill string, depending upon the point in the circuit at which it is desired to carry out analysis.

FIG. 2 shows schematically the tank 10 with a shaker 11, overflow 12 and a stirrer 13. However the shale shaker tank is commonly used as a sand settlement tank, in which case the stirrer 13 will not be present and the sample flow must be taken from nearer the surface of the tank than is shown.

A continuous slow sample flow is taken from the tank 10 under a head of 1 m through a 9 mm tube 14 leading to an averaging tank 15 with its overflow 16 to the solids control unit and a stirrer 17-which must ensure very thorough mixing in this tank, with no stagnant regions. The diameter of the tube 14 is chosen to ensure turbulent, non-clogging flow and represents perhaps the narrowest usable pipe. A wider pipe could be used with a smaller head. The tank 15 has a volume of say 0.4 or 0.5 m³. From standard flow equations the flow rate through the pipe 14 is approximately 0.014 liter/sec. which is a suitably small proportion of a typical well mud flow of 20 liter/sec. A flow rate of 0.014 liter/sec into a tank 15 of 0.4 m³ gives a residence time T of about 50 minutes.

This residence time is in fact suitable if the samples to be analysed (second samples) are taken from the tank 15 at 15 minute intervals—which is about as rapidly as can be handled if each sample is to be analysed by ion chromatography. For 15 minute sampling, the low-pass filter cut off frequency must be, to avoid aliasing, $$f_c = 1/(2 * 15 * 60).$$

Solving equation (6), with an attenuation α equal to 10 and with $w_c = 2\pi f_c$, leads to a residence time T being at least equal to 47.5 minutes.

Accordingly, for 15 minute sampling, it is satisfactory to take samples from the tank 15, for which purpose the overflow 16 may be intercepted manually or each sample may be drawn off automatically via a pipe 18 and motorized valve 19 with controller 20.

Eight hour sampling requires a much longer residence time which it is not possible to achieve with one tank 15 of sensible size. It would be possible to achieve adequate averaging by cascading a series of tanks 15, each fed by a pipe 14 from the preceding tank but it turns out that an impractically large number of tanks would be required—more than 30.

To overcome this problem the tank 15 is followed by one further tank 21 (of the same size) from which the analysis samples are taken, e.g. via a pipe 22, valve 23 and control unit 24. The tank 21 again has a vigorous stirrer 25 or other agitating means and the flow into this tank 21 is taken from the tank 15 via another 9 mm pipe 26. However the pipe 26 includes a motorized valve 27 which is opened for just 2 seconds in every minute by a control unit 28. It follows that the average flow rate from the tank 15 into the tank 21 is only 0.014/30 = 0.00047 liter/sec. The residence time in the tank 21 is multiplied by 30 in this way and the tank 21 therefore effects sufficient averaging, on top of that already effected by the tank 15, to permit analysis of 8 hour samples drawn from the tank 21, without risk of aliasing. Theoretical analysis shows that, in order to eliminate the possibility of aliasing with 8 hour sampling, the tank 15 with residence time as described above needs to be followed by a tank with a residence time of 1520 minutes. However taking into account the factor of 30 introduced by the intermittent opening of the valve 27, this comes down to a residence time of 50.6 minutes which is not significantly different from that already given above for the 0.4 m³ tank 15 fed from the 9 mm pipe 14, namely about 47.5 or 50 minutes. If necessary fine adjustment could be effected by slight variation of the time for which the valve 27 is open, the rate of opening this valve or the head from the tank 15 to the tank 21.

It is particularly important that the rate at which the valve 27 is opened—once every minute—is sufficiently high to avoid introduction of aliases on account of the sampling effected by this valve. Sampling once per minute will sample parameters correctly up to a rate of variation of ½ min⁻¹ and more rapid variation than this cannot occur at the output of the tank 15.

Although a valve could similarly be included in the pipe 14 this is undesirable if the shale shaker tank 10 is not agitated, other than by the fairly voluminous flow into the tank.

Figure 2A:
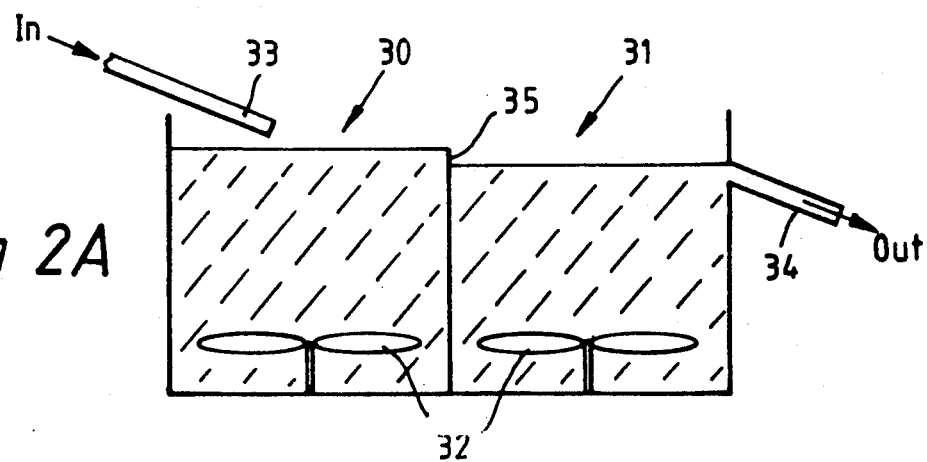
FIG. 2A illustrates a modification of part of the apparatus.

Many modifications can be made to the apparatus described. For example the pipe 14 could be taken from the overflow level of the tank 10 and the stirrer 13 be omitted. The tank 15 and/or the tank 21 could be formed as a two-compartment tank with each compartment 30, 31 (FIG. 2a) say of volume 0.5 m³, with separate stirrers 32, inflow 33 into the first compartment 30, outflow 34 (representing either outflow to the next tank or to analysis) from the second compartment 31 and a weir 35 for flow from the first compartment 30 to the second compartment 31.

Although all flows have been shown as taking place under a gravitational head, flows could equally well be via metered pumps.

Figure 3:
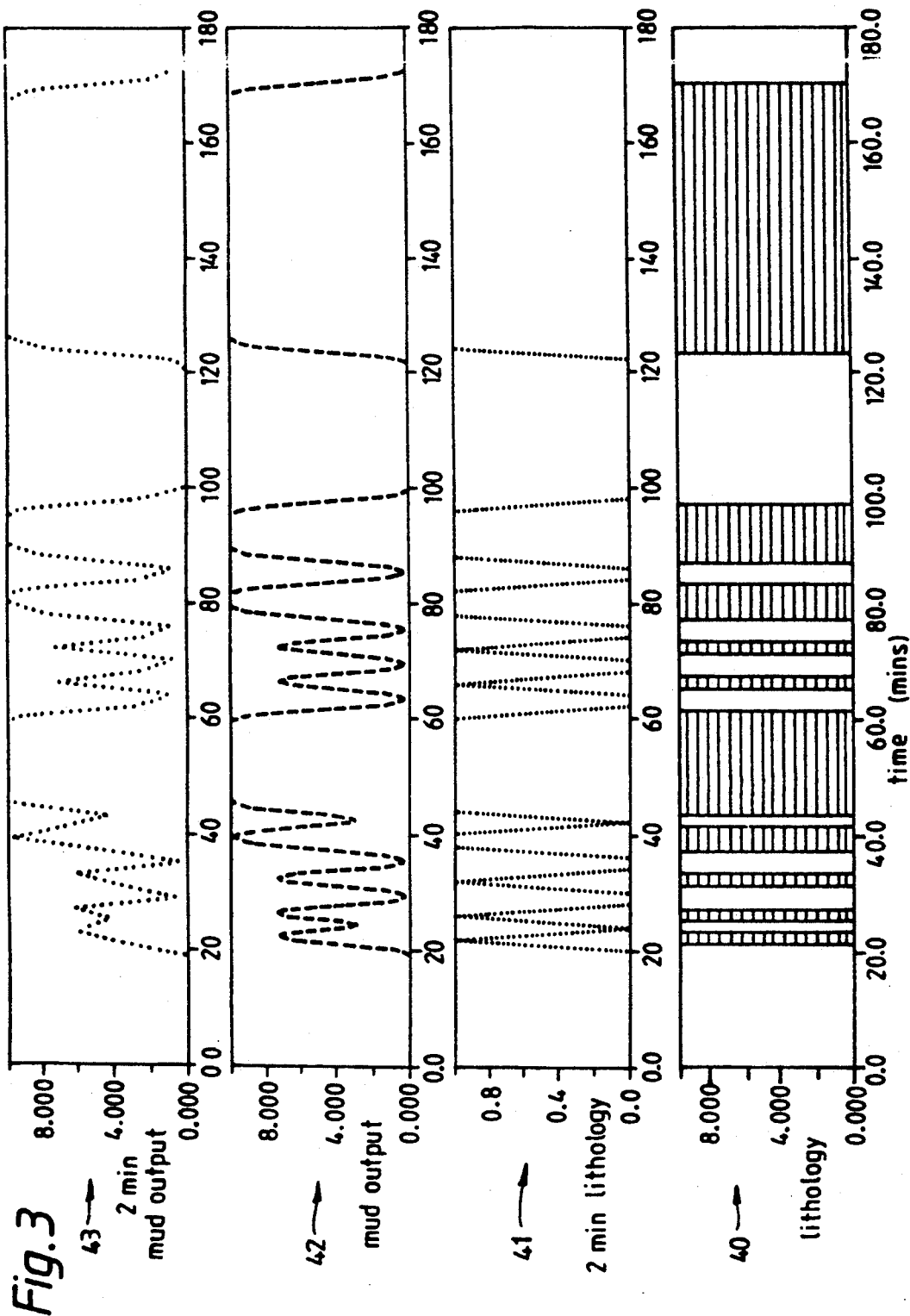
FIGS. 3 to 5 are diagrams used in explaining the effect achieved by means of the invention.
Figure 4:
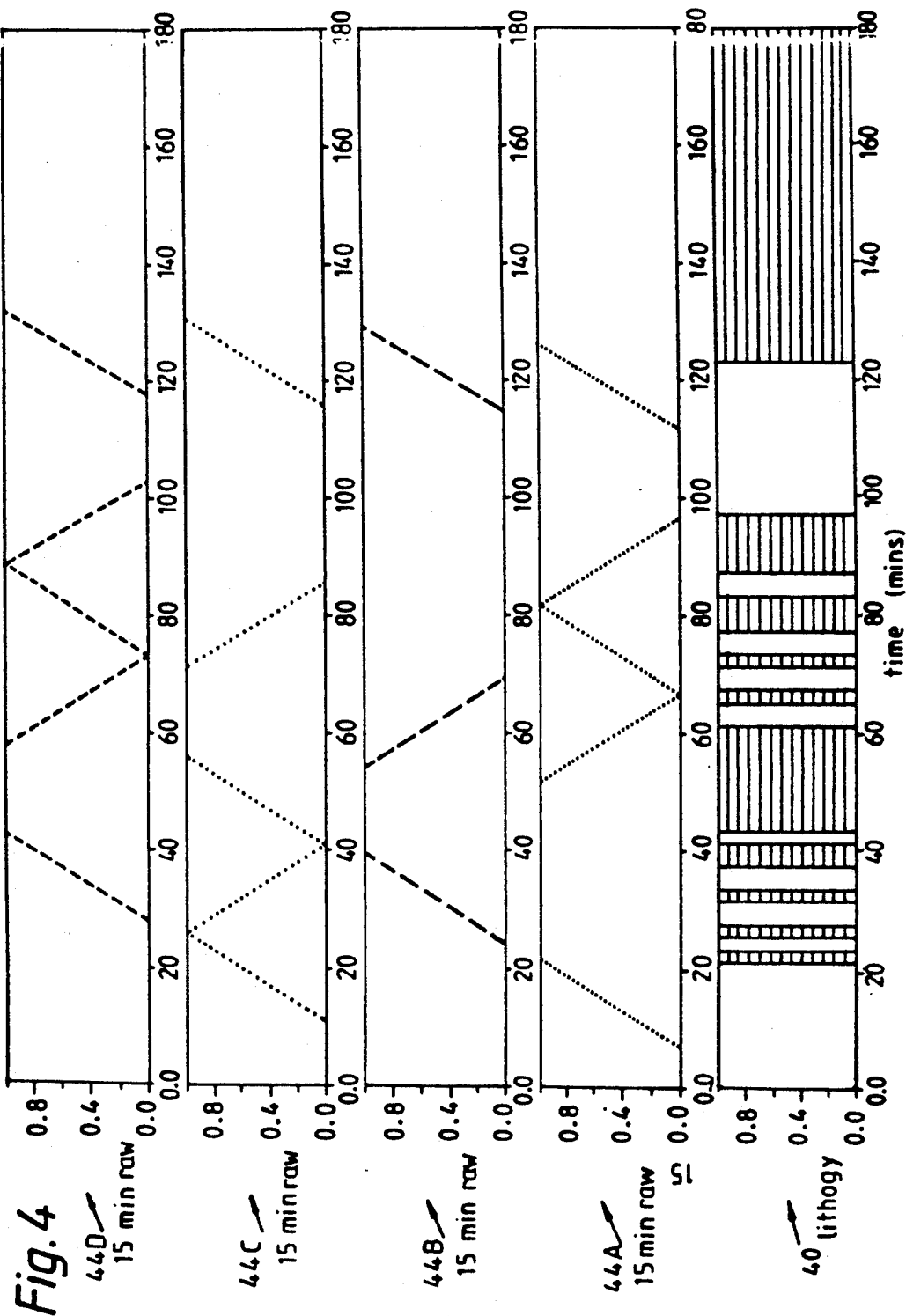
Figure 5:
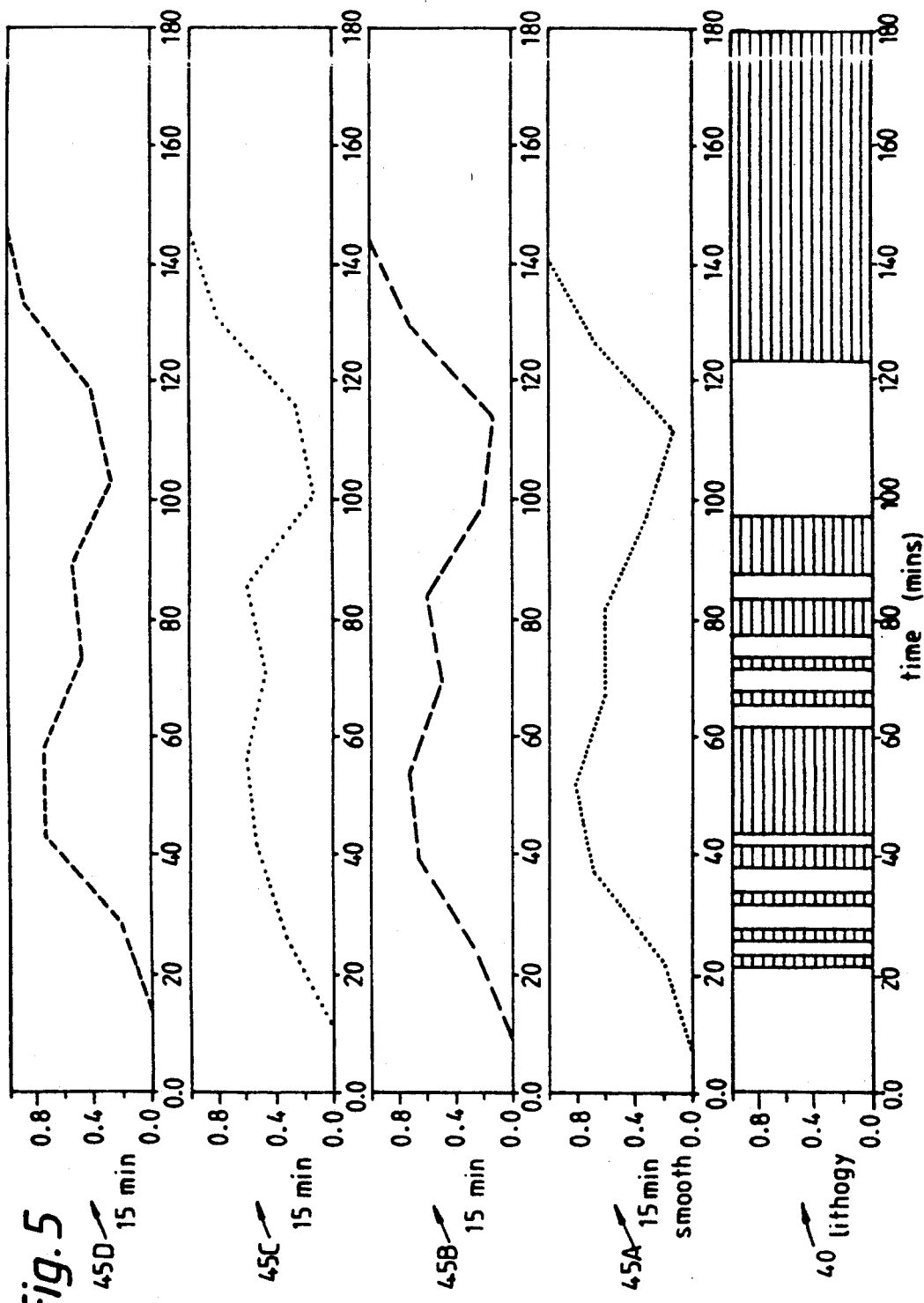

FIGS. 3 to 5 show the results of computer simulations of the results of analysis of a parameter related to a lithology 40 which comprises narrow and broad beds and causes the parameter of the mud to alternate between two values over the time scale shown as the abscissa, as indicated schematically by the alternating light and dark regions. Waveform 41 in FIG. 3 shows the results which would be obtained by sampling the mud composition at the drill bit at two-minute intervals and the lithology is naturally faithfully represented.

Waveform 42 shows the expected results of notional continuous analysis at the top of the well where the information has been smeared to some extent by hydrodynamic dispersion as the mud flows up the annulus. The salient features are nevertheless still clearly present. Finally waveform 43 shows the results of two-minute analysis at the top of the well, with the salient features still well preserved.

FIG. 4 on the other hand shows what happens when the mud is sampled, without using the present invention, at 15 minute intervals. Waveforms 44A-D show the results which would be obtained for four different analysis sequences offset by 2 minutes from one to another. It is clearly impossible to relate these results in any meaningful way to the actual lithology 40 and this is a direct consequence of aliasing-spurious and therefore useless data has been created.

FIG. 5, in contrast, shows the results to be expected when use is made of the present invention, with the 15 minute samples taken from the tank 15 in FIG. 2, having a residence time T of about 50 minutes. The four waveforms 45A-D again represent results with 2 minute offsets between the 15 minute sampling cycles. All waveforms are of approximately the same shape and relate broadly to the underlying lithology 40. The detailed lithology has been lost but it is better to have a broadly correct non-detailed lithology than a totally spurious lithology, as in FIG. 4.

Finally it should be noted that the results obtained using the invention can be enhanced. Since the nature of the averaging operation is known, an inverse operation, known as deconvolution, can be performed mathematically on the results of the analysis to sharpen up these results, even although it is impossible to recover detail fully.

A single mixing tank has a transfer function (1/T) exp(−t/T) where T is the residence time. Thus, if the input mud stream underwent a step change in some measured quantity, the output stream would show a gradual change.

Figure 6:
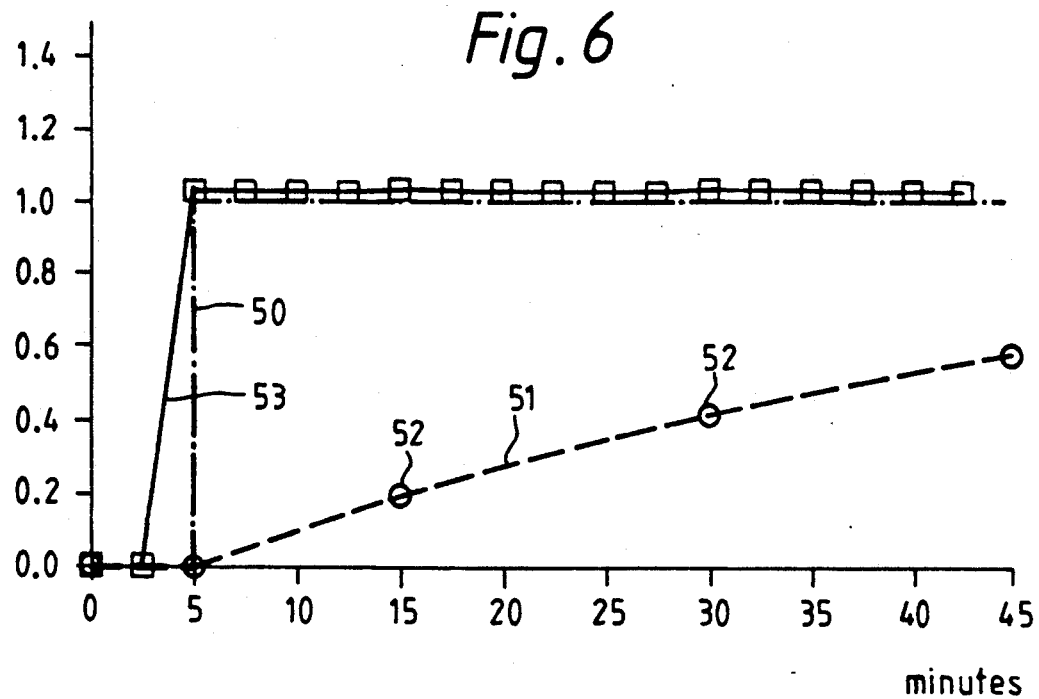
FIGS. 6 and 7 are used in explaining how data obtained using the invention can be enhanced.

These are shown in FIG. 6 where the input is the chain-dotted line 50 and the response is the broken line 51. In this example the tank has a residence time of 47 mins to permit 15 min sampling. Four sampling points 52 are shown, plus the start of the step at 5 mins.

Figure 7:
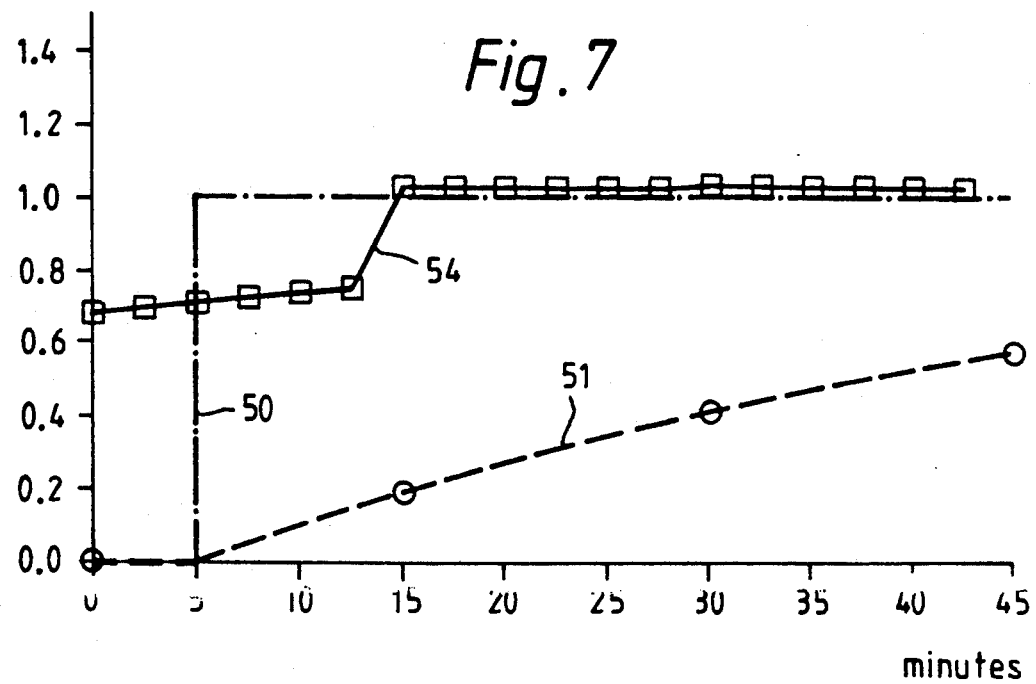

Because the transfer function of the tank is known it is feasible to deconvolve the measured points 52 and recover the original waveform as the solid line waveform 53. If the start time of the step is known then this deconvolution is virtually exact, as shown in FIG. 6. If the start time is unknown then the deconvolution cannot derive the true start time to within 7.5 mins (half the sampling time period) as shown in FIG. 7 but the deconvolution 54 is a significant improvement on the original measurements. This deconvolution can be done computationally on a continuous basis for any time varying input, not just a step.

I claim:

1. A method of sampling drilling mud which is circulating in a well and surface circulation system, the method comprising directing a sample flow comprising a part of the circulating drilling mud from the surface circulation system into an agitated container, sampling the contents of the container at a substantially regular rate, and analysing the samples, wherein the size of the container is such that the residence time of a quantity of mud corresponding to an amount removed in sampling is significant compared to the rate at which the container contents are sampled, the sample flow being a continuous sample flow taken from a first container in the surface circulation system and fed into an agitated second container from which an intermittent flow is taken into a third container, the samples to be analysed being taken from the third container.

2. A method of sampling drilling mud wherein a sample flow taken from a selected point in the mud circuit is fed into an agitated container having a capacity such that the residence time of an increment of sample flow is significant and wherein samples are taken from the container at regular intervals, the sample flow being an intermittent flow occurring with sufficient frequency to avoid introduction of aliasing.

3. A method according to claim 1, wherein the container is the last of a series of two or more agitated containers, the said sample flow being added to the first container of the series and an intermediate sample flow being passed into each container other than the first from the preceding container.

4. A method of sampling drilling mud which is circulating in a well and surface circulation system, the method comprising directing a sample flow comprising a part of the circulating drilling mud from the surface circulation system into an agitated container, sampling the contents of the container at a substantially regular rate, and analysing the samples, wherein the size of the container is such that the residence time of a quantity of mud corresponding to an amount removed in sampling is significant compared to the rate at which the container contents are sampled, and wherein the results of the analysis are enhanced by a process of inversion effected computationally and complementing the averaging introduced by the container.

5. Apparatus for sampling drilling mud comprising means for taking a sample flow from a point in the mud circuit and feeding the sample flow into a container having a capacity such that the residence time of an increment of sample flow is significant, means for agitating the mud in the container, and means for taking samples from the container at regular intervals, wherein said apparatus also comprises a further container preceding said container, said means for taking a sample flow from a point in the mud circuit feeding the sample flow into the further container, and second means for taking an intermediate sample flow from the further container and feeding it into the succeeding container, from which the samples are taken.

6. Apparatus according to claim 5, wherein the means for taking a sample flow feeds a continuous sample flow and the second means for taking a sample flow feeds an intermittent sample flow.

7. Apparatus according to claim 5, wherein the means for taking a sample flow passes mud under a gravitational head.

8. Apparatus according to claim 5, wherein the means for taking a sample flow passes mud under the action of a pump.

9. A method of sampling drilling mud which is circulating in a well and surface circulation system, the method comprising directing a sample flow comprising a part of the circulating drilling mud from the surface circulation system into an agitated container, sampling the contents of the container at a substantially regular rate, and analysing the samples, wherein the size of the container is such that the residence time of a quantity of mud corresponding to an amount removed in sampling is significant compared to the rate at which the container contents are sampled and wherein the container is the last of a series of two or more agitated containers, the said sample flow being added to the first container of the series and an intermediate sample flow being passed into each container other than the first from the preceding container.

10. A method of sampling drilling mud wherein a sample flow taken from a selected point in the mud circuit is fed into an agitated container having a capacity such that the residence time of an increment of sample flow is significant and wherein samples are taken from the container at regular intervals, further comprising the step of analysing the samples, wherein the results of the analysis are enhanced by a process of inversion effected computationally and complementing the averaging introduced by the container.

11. A method according to claim 10, wherein the container is the last of a series of two or more agitated containers, the said sample flow being added to the first container of the series and an intermediate sample flow being passed into each container other than the first from the preceding container.

12. A method according to claim 11, wherein a continuous sample flow is taken from a first container in the mud circuit and fed into an agitated second container from which an intermittent flow is taken into a third container, the samples to be analysed being taken from the third container.

13. Apparatus for sampling drilling mud which is circulating in a well and surface circulation system, the apparatus comprising means for directing a sample flow comprising a part of the circulating drilling mud from the surface circulation system into an agitated container and means for sampling the contents of the container at a substantially regular rate for analysis, wherein the size of the container is such that the residence time of a quantity of mud corresponding to an amount removed in sampling is significant compared to the rate at which the container contents are sampled, said apparatus comprising a series of two or more agitated containers, wherein said container is the last of the series, said means for directing a sample flow comprises first means directing said part of the circulating drilling mud to a first container of the series and second means being provided for directing an intermediate sample flow into each container other than the first from a preceding container.

14. Apparatus according to claim 13, wherein the first means for taking a sample flow feeds a continuous sample flow and the second means for taking a sample flow feeds an intermittent sample flow.

* * * * *